(12) United States Patent
DePaula

(10) Patent No.: US 8,288,344 B2
(45) Date of Patent: Oct. 16, 2012

(54) CERAMIC COMPOSITION FOR FILLING BONE DEFECTS

(75) Inventor: Carl Alexander DePaula, Cranbury, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 1069 days.

(21) Appl. No.: 11/724,255

(22) Filed: Mar. 15, 2007

(65) Prior Publication Data

US 2008/0226688 A1 Sep. 18, 2008

(51) Int. Cl.
*A61P 19/08* (2006.01)
*A61K 38/00* (2006.01)
*C07K 14/475* (2006.01)
*C12N 5/071* (2010.01)

(52) U.S. Cl. ......... 514/16.7; 514/7.6; 514/9.1; 435/366; 606/908; 606/909; 606/910

(58) Field of Classification Search .................. None
See application file for complete search history.

(56) References Cited

U.S. PATENT DOCUMENTS

| 5,073,373 | A | 12/1991 | O'Leary et al. | |
|---|---|---|---|---|
| 5,120,340 | A * | 6/1992 | Ducheyne et al. | 65/17.5 |
| 5,290,558 | A | 3/1994 | O'Leary et al. | |
| 5,356,629 | A | 10/1994 | Sander et al. | |
| 5,522,893 | A | 6/1996 | Chow et al. | |
| 6,030,635 | A | 2/2000 | Gertzman et al. | |
| 6,437,018 | B1 | 8/2002 | Gertzman et al. | |
| RE38,522 | E | 5/2004 | Gertzman et al. | |
| 2007/0123996 | A1 * | 5/2007 | Sugaya et al. | 623/23.51 |
| 2008/0069852 | A1 * | 3/2008 | Shimp et al. | 424/423 |
| 2008/0147197 | A1 * | 6/2008 | McKay | 623/23.51 |
| 2008/0221701 | A1 * | 9/2008 | Zhong et al. | 623/23.62 |

* cited by examiner

*Primary Examiner* — Xiaozhen Xie
(74) *Attorney, Agent, or Firm* — Jones Day

(57) ABSTRACT

The invention is directed toward a sterile formable implant composition for application to a bone defect site comprising bioactive glass particles in an aqueous carrier solution, the bioactive glass particles being added to a viscous carrier at a concentration ranging from about 68% to about 76% (w/w), the carrier comprising a mixture of glycerol and polyethylene glycol ranging from 24% to 32% (w/w) with the ratio of glycerol to polyethylene glycol ranging from about 45:55 to about 65:35.

31 Claims, 2 Drawing Sheets

| Sample # | Carrier % | Carrier ratio | Glycerol Calc. (g) | Glycerol Actual (g) | PEG 2000 Calc. (g) | PEG 2000 Actual (g) | NovaBone glass % | NovaBone glass Calc. (g) | NovaBone glass Actual (g) | NovaBone powder % | NovaBone powder Calc. (g) | NovaBone powder Actual (g) | Avg. penetration | Avg. pH |
|---|---|---|---|---|---|---|---|---|---|---|---|---|---|---|
| 1 | 31 | 45:55 | 2.790 | 2.791 | 3.410 | 3.410 | 56 | 11.2 | 11.20 | 13 | 2.6 | 2.60 | 33.25 | 11.83 |
| 2 | 31 | 45:55 | 2.790 | 2.793 | 3.410 | 3.412 | 57 | 11.4 | 11.40 | 12 | 2.4 | 2.40 | 41.00 | 11.93 |
| 3 | 31 | 45:55 | 2.790 | 2.790 | 3.410 | 3.410 | 55 | 11.0 | 11.00 | 14 | 2.8 | 2.80 | 39.67 | 11.89 |
| 4 | 30 | 45:55 | 2.700 | 2.703 | 3.300 | 3.303 | 56 | 11.2 | 11.20 | 14 | 2.8 | 2.80 | 39.67 | 11.92 |
| 5 | 30 | 45:55 | 2.700 | 2.700 | 3.300 | 3.300 | 57 | 11.4 | 11.40 | 13 | 2.6 | 2.60 | 37.75 | 11.87 |
| 6 | 32 | 45:55 | 2.880 | 2.885 | 3.520 | 3.524 | 56 | 11.2 | 11.20 | 12 | 2.4 | 2.40 | 45.00 | 12.00 |
| 7 | 32 | 45:55 | 2.880 | 2.883 | 3.520 | 3.523 | 55 | 11.0 | 11.00 | 13 | 2.6 | 2.60 | 43.75 | 11.95 |
| 8 | 31 | 47:53 | 2.914 | 2.914 | 3.286 | 3.286 | 56 | 11.2 | 11.20 | 13 | 2.6 | 2.60 | 42.25 | 11.81 |
| 9 | 31 | 43:57 | 2.666 | 2.664 | 3.534 | 3.533 | 56 | 11.2 | 11.20 | 13 | 2.6 | 2.60 | 35.75 | 11.84 |
| 10 | 31 | 35:65 | 2.170 | 2.170 | 4.030 | 4.030 | 56 | 11.2 | 11.20 | 13 | 2.6 | 2.60 | 25.25 | 12.06 |
| 11 | 31 | 70:30 | 4.340 | 4.340 | 1.860 | 1.860 | 56 | 11.2 | 11.20 | 13 | 2.6 | 2.60 | 61.75 | 11.32 |
| 12 | 31 | 45:55 | 2.790 | 2.790 | 3.410 | 3.410 | 61 | 12.2 | 12.20 | 8 | 1.6 | 1.60 | 41.67 | 11.80 |
| 13 | 31 | 45:55 | 2.790 | 2.790 | 3.410 | 3.410 | 51 | 10.2 | 10.20 | 18 | 3.6 | 3.60 | 39.67 | 11.90 |
| 14 | 31 | 50:50 | 3.100 | 3.100 | 3.100 | 3.101 | 56 | 11.2 | 11.20 | 13 | 2.6 | 2.60 | 48.67 | 11.72 |
| 15 | 31 | 40:60 | 2.480 | 2.480 | 3.720 | 3.720 | 56 | 11.2 | 11.20 | 13 | 2.6 | 2.60 | 32.33 | 12.00 |

Fig. 1

| Sample # | Avg. Pen. before gamma | Avg. Pen. after gamma | Δ Pen. | Avg. pH before gamma | Avg. pH after gamma | Δ pH |
|---|---|---|---|---|---|---|
| 1 | 33.25 | 52.67 | 19.42 | 11.83 | 11.85 | 0.02 |
| 2 | 41.00 | 50.00 | 9.00 | 11.93 | 11.77 | -0.16 |
| 3 | 39.67 | 50.67 | 11.00 | 11.89 | 11.61 | -0.28 |
| 4 | 39.67 | 47.00 | 7.33 | 11.92 | 11.75 | -0.17 |
| 5 | 37.75 | 47.67 | 9.92 | 11.87 | 11.53 | -0.34 |
| 6 | 45.00 | 54.33 | 9.33 | 12.00 | 11.58 | -0.42 |
| 7 | 43.75 | 53.00 | 9.25 | 11.95 | 11.53 | -0.42 |
| 8 | 42.25 | 47.00 | 4.75 | 11.81 | 11.61 | -0.20 |
| 9 | 35.75 | 49.33 | 13.58 | 11.84 | 11.64 | -0.20 |
| 10 | 25.25 | 31.00 | 5.75 | 12.06 | 11.65 | -0.41 |
| 11 | 61.75 | 70.75 | 9.00 | 11.32 | 11.15 | -0.17 |
| 12 | 41.67 | 50.00 | 8.33 | 11.80 | 11.56 | -0.24 |
| 13 | 39.67 | 49.00 | 9.33 | 11.90 | 11.64 | -0.26 |
| 14 | 48.67 | 52.00 | 3.33 | 11.72 | 11.38 | -0.34 |
| 15 | 32.33 | 43.50 | 11.17 | 12.00 | 11.70 | -0.30 |

Fig.2

CERAMIC COMPOSITION FOR FILLING BONE DEFECTS

RELATED APPLICATIONS

There is no related application.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention is generally directed toward a surgical bioactive glass bone implant product and more specifically is a moldable and shapeable putty composition sterilized by gamma radiation for filling bone defects having a bioactive glass material with a size ranging from 32 to 710 μm with a weight ranging from 68% to 76% by weight of the composition mixed in a fluid carrier of glycerol and polyethylene glycol.

2. Background of the Invention

Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Formable compositions are used to correct surgical defects that may be caused by trauma, pathological disease, surgical intervention or other situations where defects need to be managed in osseous surgery. It is important to have the defect filler in the form of a stable, viscous formable composition to facilitate the placement of the composition into the surgical site which is usually uneven in shape and depth. The surgeon will take the composition on a spatula or other instrument and trowel it into the site or take it in his/her fingers to shape the bone defect material into the proper configuration to fit the site being corrected. It is also important that the defect filler be biocompatible.

Osteogenic bone grafting materials may generally be separated into two classes, namely those which are osteoconductive, and those which are osteoinductive. It can be said that osteoconductive implants "conduct" bone growth across defects when implanted into osseous tissue. Osteoinductive implants, on the other hand, have the ability to "induce" cells in the area to generate bone of their own accord. These osteoinductive implants will cause the generation of bone even when they are implanted into non-osseous tissue.

Many products have been developed in an attempt to treat this surgical need for a biocompatible formable material. One such example is autologous bone particles or segments recovered from the patient. When removed from the patient, the segments or bone particles are wet and viscous from the associated blood. This works very well to heal the defect but requires significant secondary surgery resulting in lengthening the surgery, extending the time the patient is under anesthesia and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Allograft bone is a logical substitute for autologous bone. It is readily available and precludes the surgical complications and patient morbidity associated with autologous bone as noted above. Allograft bone is essentially a collagen fiber reinforced hydroxyapatite matrix containing active bone morphogenic proteins (BMP) and can be provided in a sterile form.

Demineralized Bone Matrix (DBM) was first described by Senn in 1889. It was rediscovered and thoroughly studied by Urist and Strates in the late 1960 3 s. It has since become a major product of tissue banks around the world. As the name implies, it is bone which has been demineralized by treatment with acid. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a gel, GRAFTON®, a registered trademark of Osteotech Inc., which is a simple mixture of glycerol and lyophilized, demineralized bone powder of a particle size in the range of 0.1 cm to 1.2 cm (1000 microns to 12,000 microns) as is disclosed in U.S. Pat. No. 5,073,373. GRAFTON works well to allow the surgeon to place the allograft bone material at the site.

However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material with a glycerol carrier to be runny and to flow away from the site almost immediately after placement which prevents the proper retention of the bone material within the site as carefully placed by the surgeon.

U.S. Pat. No. 5,290,558 discloses a flowable demineralized bone powder composition using an osteogenic bone powder with large particle size ranging from about 0.1 to about 1.2 cm mixed with a low molecular weight polyhydroxy compound possessing from 2 to about 18 carbons including a number of classes of different compounds such as monosaccharides, disaccharides, water dispersible oligosaccharides and polysaccharides.

U.S. Pat. No. 5,356,629 discloses making a rigid composition in the nature of a bone cement to fill defects in bone by mixing biocompatible particles preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder, in addition to morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used. This is simply a cement used for implantation of hip prosthesis and is not used to promote bone growth.

U.S. Pat. No. 6,437,018 issued Aug. 20, 2002 owned by the assignee of the present invention discloses a malleable bone putty and a flowable gel composition for application to a bone defect site to promote new bone growth at the site using demineralized lyophilized allograft bone powder. The bone powder has a particle size ranging from about 100 to about 850 microns and is mixed in a high molecular weight hydrogel carrier containing a sodium phosphate saline buffer, the hydrogel component of the carrier ranging from about 0.75 to 4.5% of the composition and having a molecular weight of about at least 160,000 Daltons. The composition has a pH between 6.8-7.4, contains about 25% to about 35% bone powder and can be additionally provided with BMP's. Another malleable bone putty is disclosed in U.S. Pat. No. 6,030,635, now RE 38,522, issued Feb. 29, 2000.

Another product group involves the use of inorganic materials to provide a matrix for new bone to grow at the surgical site. These inorganic materials include hydroxyapatite obtained from sea coral or derived synthetically. Either form may be mixed with the patient's blood and/or bone marrow to form a gel or a putty. Calcium sulfate or plaster of Paris may be mixed with water to similarly form a putty. Other products within this group include ceramics such as tricalcium phosphate.

The use of ceramic compositions utilizing beta tricalcium phosphate and alpha tricalcium phosphate (TCP) for bone graft substitutes are also well known in the art. These graft materials generally harden in place. U.S. Pat. No. 5,522,893 issued Jun. 4, 1996 discloses a bone filling material which is a combination of tricalcium phosphate and dicalcium phosphate salts that are mixed and react to harden and form hydroxycarbonate apatite after implantation. The prior art TCP compositions tend to harden rather quickly and have short if any shelf life. Thus, the composition has to be mixed at the time of surgery or in a short time period before the time of surgery.

Bioglass® and other bioactive glass is a bone grafting material composed of $SiO_2$, $Na_2O$, $CaO$, $P_2O_5$ glass which has the ability to produce a bio-active surface layer of hydroxyapatite carbonate within minutes of implantation. This material does not rely on donor availability and overcomes cultural and religious qualms or prohibitions about using human bone. Furthermore, the material has osteoinductive and osteoconductive characteristics and a long shelf life which allow it to be successfully used as bone implant repair material.

SUMMARY OF THE INVENTION

The subject formulation is a specific mixture of bioactive glass particles and powder mixed in a carrier of glycerol and polyethylene glycol.

An inventive aspect of this composition is overcoming handling problems while preserving a favorable biologic response by controlling the particle size of the glass particles and the weight percentage in the composition by mixing the same in the biocompatible carrier. The favorable handling characteristics of the putty are due to the narrow range of the percentage of glass weight in the composition and the carrier composition. Glass particle sizes that are larger than those of the present invention create a putty with a gritty feel which is unacceptable to a surgeon and cannot be effectively used in a syringe. Smaller glass particle sizes create a putty with an unfavorable biologic response because the small particles under 20 μm can be absorbed too quickly and lose their efficacy, could cause an immunological response, and could migrate though the lymphatic system.

It is an object of the invention to utilize a bioactive glass defect material having a particle size that is useful to achieve the malleability characteristics of a putty composition in that it holds shape and does not melt during handling which results in easy application allowing easy insertion by the surgeon into the bone defect area.

It is also an object of the invention to create a bioactive glass defect repair material which can be easily handled by the physician and maintains integrity after the implant until the surgical site is closed and stays in place during irrigation.

It is another object of the invention that the composition is ready to use out of the package and requires no mixing.

It is another object of the invention to utilize a carrier which degrades rapidly to expose the bioactive glass for osteostimulatory bone healing.

It is still another object of the invention to create a bioactive glass defect material repair which is stable and has an extended shelf life of two years when packaged.

It is another object of the invention to create a bioactive glass defect repair material which additionally uses cellular material such as living cells and cell elements.

It is yet another object of the invention to use a growth factor in the bioactive glass defect repair material.

It is still another object of the invention to use an anti-infective agent in the bioactive glass defect repair material.

These and other objects, advantages, and novel features of the present invention will become apparent when considered with the teachings contained in the detailed disclosure along with the accompanying drawings.

BRIEF DESCRIPTION OF THE DRAWINGS

FIG. 1 shows a chart reflecting a series of putty samples which were tested prior to gamma radiation sterilization; and FIG. 2 shows a chart reflecting testing of the samples of FIG. 1 before and after sterilization with gamma radiation.

DESCRIPTION OF THE INVENTION

The present invention is directed towards a bioactive glass particle based putty composition mixed in a glycerol and polyethylene glycol carrier which is applied to bone defects. The carrier degrades in less than three days after implant to expose the bioactive glass particles for osteostimulatory bone healing.

The particle size of glass particles when mixed with high molecular weight carrier of glycerol and polyethylene glycol carrier produces clinically useful bone inducing properties. It should be noted that when glycerol and polyethylene glycol were used separately as the carrier that the moldability and shape holding ability of the composition was inferior to that of the present composition. The formability property of the combined carrier and bioactive glass weight and size permits the surgeon to shape the composition to exactly fit the surgical defect. Manipulation of the lump of formable bioactive glass composition may be done without it sticking to the gloves of the surgeon, behaving somewhat like a wet clay used in sculpting.

It is an important aspect of the present invention that the implant matrix must remain at the wound site and not be washed away by the flowing blood and other irrigation fluids brought to the site by the healing mechanism. While viscous, the glycerol and polyethylene glycol carrier is a high molecular weight macromolecule and is not readily dissolved and washed away by the blood and fluids at the wound site but does degrade rapidly within the defect site to expose the bioactive glass for osteostimulatory bone healing.

Thus, the therapeutic formable bioactive glass composition will not be dissipated by being washed away and will be present at the defect site to be osteoconductive and osteoinductive. The amount of bioactive glass is maximized to achieve the optimum balance of osteoconductivity and physical handling properties. Adding too much bioactive glass may create a gritty or sandy condition in which the composition is not enclosed by the surrounding viscous matrix and the glass particles are not held together. The preferred type of bioactive glass material used in the invention is 45s5 bioactive glass (Bioglass®) having a particle size ranging from 92 μm to 710 μm mixed in a ratio with bioactive glass powder having a size ranging from 32 μm to 90 μm.

The primary role of a carrier is to serve as a delivery vehicle for the bioactive glass. The bulk viscosity of the carrier achieves the design goal of good handling properties by balancing the molecular weight and concentration used in the formulation.

The putty is preferably formulated with a weight ranging from 68% to 76% bioactive glass particles w/w (preferably about 68% to about 70%) comprising a combination of glass particles manufactured by Novabone Inc. ranging in size from 90 μm to 710 μm mixed with glass powder also manufactured by Novabone Inc. ranging in size from 32 μm to 90 μm in a ratio from 3:5 to about 5.0 together with a 24% to 32% (wt %) glycerol and polyethylene glycol (PEG) carrier. The ratio of glycerol to PEG preferably runs from 35:65 to 60:40; (preferably about 45:55 to about 50:50) with the total carrier ranging from about 24% to about 32% (preferably about 30% to about 32%) by weight of the composition. Particles less than 20 microns are undesirable because they can cause an inflammatory response and the small particles can migrate through the lymphatic system.

In the present formulation, a range of 68% to 70% bioactive glass was the most preferred range with being selected as the optimum glass material weight formulation. A one week accelerated aging study was performed at 40° C. (equivalent to 4 weeks at ambient temperatures) on the putty composition and there was no change in the putty. The penetration, pH and handling of the preferred putty did not change from time zero to one week accelerated aging.

Materials Used:

1. Novabone 45s5 bioactive glass ($SiO_2Na_2OCaOP_2O_5$) 90 μm to 710 μm in size manufactured by Novabone Products LLC. The composition by weight is:

| | |
|---|---|
| $SiO_2$ | 45% |
| $Na_2O$ | 24.5% |
| CaO | 24.5% |
| $P_2O_5$ | 6.0% | with a tolerance of about ±2.0%. It has a density of 2.73 grams/cc and a softening point of 627° C.

2. Novabone 45s5 bioactive glass power ($SiO_2Na_2OCaOP_2O_5$) 32 μm to 90 μm in size sieved to remove powder less than 32 μm.

3. Glycerol manufactured by EMD Chemicals, Inc.

4. Polyethylene glycol (PEG) manufactured by Clariant Corporation having a molecular weight ranging from 1000 to 2000 Daltons, preferably 1500 and 2000 Daltons.

The PEG was melted in a water bath and then mixed with glycerol.

Additives which are beneficial to bone growth and which are additionally added into the formable composition are living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells. These cells or cell elements or combinations of the same are present at a concentration of $10^5$ to $10^8$ per cc of carrier and are added into the composition at time of surgery.

Growth factor additives which can be used in the present invention either at the time of packaging or at surgery depending on the stability of the growth factor are transforming growth factor (TGF-beta), insulin growth factor (IGF-1); platelet derived growth factor (PDGF), vascular endothelial growth factor (VEGF), fibroblast growth factor (FGF) (numbers 1-23) and variants thereof, osteopontin, growth hormones such as somatotropin cellular attractants and attachment agents and bone morphogenic proteins (BMP's). Fiberblast growth factor is added in the amount of 2 to 4 milligrams per 10 cc of carrier solution.

Any number of medically useful substances can be used in the invention by adding the substances to the composition at any steps in the mixing process or directly to the final composition. Such substances include Type I collagen and insoluble collagen derivatives for blood vessel formation and/or bone formation, hydroxyapatite, and soluble solids and/or liquids dissolved therein.

Also included in the additives which may be added to the carrier are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin.

It is also envisioned that other additives which can be added to the composition are amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments.

Food (glucose) for the cells noted above could be added along with amino acids. It is also envisioned that one could add additional glycosaminoglycans (GAGs) or proteoglycans to further improve and speed bone formation (the specific GAGs of physiological significance are hyaluronic acid, dermatan sulfate, chondroitin sulfate, heparin, heparan sulfate, and keratan sulfate). In addition, carboxymethylcellulose could be added to the formulation to provide additional elasticity to the putty for improved handling or other surgical applications.

In the following examples, various compositions were formulated to determine initial product usefulness. These compositions were not sterilized by gamma radiation:

EXAMPLE 1

Unacceptable Putty Composition Formulation

A putty composition was formulated by mixing 6.5 g of bioactive glass particles (90 µm to 710 µm) (65% w) and 1 g of bioactive glass powder (32 µm to 90 µm) (10% w) with 2.5 g of carrier (25% w) made up of glycerol and PEG having a molecular weight of 2000 in a ratio of 50:50. The composition had a total glass percentage (75% w) forming a putty which was very sticky and unacceptable.

EXAMPLE 2

Unacceptable Putty Composition Formulation

A putty composition was formulated by mixing 6.5 g of bioactive glass particles (90 µm to 710 µm) (57% w) and 2.5 g of bioactive glass powder (32 µm to 90 µm) (22% w) with 2.5 g of carrier (22% w) made up of glycerol and PEG having a molecular weight of 1500 in a ratio of 50:50. The composition had a total glass percentage (79% w) forming a putty which was dry and grainy and unacceptable.

EXAMPLE 3

Acceptable Putty Composition Formulation

A putty composition was formulated by mixing 6.5 g of bioactive glass particles (90 µm to 710 µm) (62% w) and 1.5 g of bioactive glass powder (32 µm to 90 µm) (14% w) with 2.4 g of carrier (24% w) made up of glycerol and PEG having a molecular weight of 2000 in a ratio of 60:40. The composition had a total glass percentage (76% w) forming a putty which was acceptable.

EXAMPLE 4

Acceptable Putty Composition Formulation

A putty composition was formulated by mixing 6.5 g of bioactive glass particles (90 µm to 710 µm) (62% w) and 1.5 g of bioactive glass powder (32 µm to 90 µm) (14% w) with 3.0 g of carrier (27% w) made up of glycerol and PEG having a molecular weight of 1500 in a ratio of 60:40. The composition had a total glass percentage (76% w) forming a putty which was good and acceptable.

EXAMPLE 5

Unacceptable Putty Composition Formulation

A putty composition was formulated by mixing 6.5 g of bioactive glass particles (90 µm to 710 µm) (62% w) and 1.5 g of bioactive glass powder (32 µm to 90 µm) (14% w) with 3.0 g of carrier (27% w) made up of glycerol and PEG having a molecular weight of 2000 in a ratio of 70:30. The composition had a total glass percentage (76% w) forming a putty which was tacky and unacceptable.

EXAMPLE 6

Unacceptable Putty Composition Formulation

A putty composition was formulated by mixing 6.5 g of bioactive glass particles (90 µm to 710 µm) (62% w) and 1.5 g of bioactive glass powder (32 µm to 90 µm) powder (14% w) with 3.0 g of carrier (27% w) made up of glycerol and PEG having a molecular weight of 1500 in a ratio of 70:30. The composition had a total glass percentage (76% w) forming a putty which was tacky and unacceptable.

EXAMPLE 7

Unacceptable Putty Composition Formulation

A putty composition was formulated by mixing 6.0 g of bioactive glass particles (90 µm to 710 µm) (57% w) and 1.5 g of bioactive glass powder (32 µm to 90 µm) (14% w) with 3.0 g of carrier (29% w) made up of glycerol and PEG having a molecular weight of 1500 in a ratio of 65:35. The composition had a total glass percentage (71% w) forming a putty which was grainy and unacceptable.

EXAMPLE 8

Acceptable Putty Composition Formulation

A putty composition was formulated by mixing 5.5 g of bioactive glass particles (90 µm to 710 µm) (53% w) and 2.0 g of bioactive glass powder (32 µm to 90 µm) (19% w) with 3.0 g of carrier (30% w) made up of glycerol and PEG having a molecular weight of 1500 in a ratio of 65:35. The composition had a total glass percentage (71% w) forming a putty which was good and acceptable.

EXAMPLE 9

Unacceptable Putty Composition Formulation

A putty composition was formulated by mixing 6.0 g of bioactive glass particles (90 µm to 710 µm) (56% w) and 1.8 g of bioactive glass powder (32 µm to 90 µm) (17% w) with 3.0 g of carrier (28% w) made up of glycerol and PEG having a molecular weight of 2000 in a ratio of 65:35. The composition had a total glass percentage (73% w) forming a putty which was grainy and unacceptable.

EXAMPLE 10

Acceptable Putty Composition Formulation

A putty composition was formulated by mixing 5.5 g of bioactive glass particles (90 µm to 710 µm) (51% w) and 1.9 g of bioactive glass powder (32 µm to 90 µm) (17% w) with 3.5 g of carrier (32% w) made up of glycerol and PEG having a molecular weight of 2000 in a ratio of 65:35. The composition had a total glass percentage (68% w) forming a putty which was very good and acceptable.

Another series of formulated putty samples which were subjected to gamma radiation sterilization were tested as can be seen in FIG. 1. The testing took place on 15 samples having a carrier weight of 30% to 32% with a carrier composition ratio ranging from about 45% glycerol to about 55% PEG 2000 (11 samples; #1-9, 12 and 13); 35% glycerol to 65% PEG 2000 (1 sample, #10); 70% glycerol to 30% PEG 2000 (1 sample, #11); 50% glycerol to 50% PEG 2000 (1 sample, #14) and 40% glycerol to 60% PEG 2000 (1 sample #15). The glass particles (90 µm to 710 µm) ranged from 51% to 61% in total weight and glass powder (32 µm to 90 µm) ranged from 8% to 18%.

Samples #1-6 were firm, moldable and held to shape well (note sample #1 was the nominal sample); samples #7-9 were softer than those of the nominal sample but acceptable.

Sample #10 was stiff to firm and not acceptable; sample #11 was not moldable at all and samples #12, 13 and 15 were softer than the nominal (sample #1) but acceptable and sample #14 was the best putty being very soft and moldable.

The putty mixture was then subjected to gamma sterilization of 30+ or −5 kGy. The gamma radiation sterilization did not affect the performance of the glass (osteoinductiveness) unlike that of bone when it is radiated so that the osteostimulatory properties of the same are not changed. The gamma radiation does, however, change the handling properties of the putty making it softer as can be seen by the chart of FIG. 2. This is believed to occur, because the gamma radiation cleaves the PEG molecules lowering its molecular weight and reducing its melting temperature. This softening was quantified by measuring permeation. It should also be noted that there were slight changes in the pH after treatment.

The resultant putty composition preferably had 68% to 70% bioglass by weight with the carrier ranging from 30% to 32% by weight.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claimed is:

1. A composition for application to a bone defect site comprising bioactive glass and a carrier, wherein said bioactive glass is present in an amount ranging from about 68% to about 70% (w/w) of the composition; wherein the carrier comprises a mixture of glycerol and polyethylene glycol present in a ratio of glycerol to polyethylene glycol ranging from about 45:55 to about 65:35, wherein the carrier is present in an amount ranging from about 24% to about 32% (w/w) of the composition; and wherein the composition is malleable during application of the composition to the bone defect.

2. The composition of claim 1, wherein said bioactive glass comprises units ranging in size from 32 microns to 710 microns.

3. The composition of claim 1, wherein said bioactive glass comprises (a) glass particles and (b) glass powder, wherein said glass powder ranges from 32 µm to 90 µm in size.

4. The composition of claim 1, wherein said bioactive glass comprises glass particles ranging from 90 µm to 710 µm in size and glass powder ranging from 32 µm to 90 µm in size.

5. The composition of claim 1, wherein said bioactive glass comprises glass particles ranging from 90 µm to 710 µm in size and glass powder ranging from 32 µm to 90 µm in size, and wherein said glass particles and said glass powder are present in a ratio of glass particles to glass powder ranging from about 3.5:1 to about 5:1.

6. The composition of claim 1, wherein said bioactive glass comprises glass particles ranging from 90 µm to 710 µm in size and glass powder ranging from 32 µm to 90 µm in size, and wherein said glass particles are present in an amount ranging from about 53% to about 62% (w/w) of the composition.

7. The composition of claim 1, wherein said bioactive glass comprises glass particles ranging from 90 µm to 710 µm in size and glass powder ranging from 32 µm to 90 µm in size, and wherein said glass powder is present in an amount ranging from about 12% to about 19% (w/w) of the composition.

8. The composition of claim 1, wherein said glycerol and said polyethylene glycol are present in a ratio of glycerol to polyethylene glycol of about 50:50.

9. The composition of claim 1, further comprising a growth factor additive, wherein said growth factor additive comprises a transforming growth factor, an insulin growth factor, a platelet derived growth factor, a vascular endothelial growth factor, a fibroblast growth factor, osteopontin, a growth hormone, somatotropin, or combinations thereof.

10. The composition of claim 1, further comprising a growth factor additive wherein said growth factor additive comprises a fibroblast growth factor, a variant thereof, or combinations thereof in an amount of 2 to 4 milligrams per 10 cc of carrier.

11. The composition of claim 1, further comprising an antiviral additive, an antimicrobial, an antibiotic, or combinations thereof, wherein said antiviral additive comprises one or more of an antiviral additive that is effective against HIV and hepatitis, and wherein said antimicrobial or antibiotic comprises one or more of erythromycin, bacitracin, neomycin, penicillin, polymyxin B, tetracycline, viomycin, chloromycetin, streptomycin, cefazolin, ampicillin, azactam, tobramycin, clindamycin, or gentamycin.

12. The composition of claim 1, further comprising living cells.

13. The composition of claim 12, wherein the living cells comprise chondrocytes, platelets, blood plasma, bone marrow cells, mesenchymal stem cells, pluripotential cells, osteoblasts, fibroblasts, or combinations thereof.

14. The composition of claim 13, wherein the living cells are present in an amount ranging from $10^5$ to $10^8$ per cc of the carrier.

15. The composition of claim 1, wherein the composition is a putty.

16. A composition for application to a bone defect site comprising bioactive glass and a carrier, wherein said bioactive glass is present in an amount ranging from about 68% to about 70% (w/w) of the composition, and wherein said bioactive glass comprises glass particles ranging from 90 µm to 710 µm in size; wherein the carrier comprises a mixture of glycerol and polyethylene glycol, wherein the carrier is present in an amount ranging from about 24% to about 32% (w/w) of the composition, and wherein said glycerol and said polyethylene glycol are present in a ratio of glycerol to polyethylene glycol ranging from about 45:55 to about 65:35; and wherein the composition is malleable during application of the composition to the bone defect.

17. The composition of claim 16, wherein the bioactive glass further comprises glass powder which ranges from 32 µm to 90 µm in size, and wherein said glass particles and said glass powder are present in a ratio of glass particles to glass powder ranging from about 3.5:1 to about 5:1.

18. The composition of claim 16, further comprising a growth factor additive, wherein said growth factor additive comprises a transforming growth factor, an insulin growth factor, a platelet derived growth factor, a vascular endothelial growth factor, a fibroblast growth factor, osteopontin, a growth hormone, somatotropin, or combinations thereof.

19. The composition of claim 16, further comprising a growth factor additive wherein said growth factor additive comprises a fibroblast growth factor, a variant thereof, or combinations thereof in an amount of 2 to 4 milligrams per 10 cc of carrier.

20. The composition of claim 16, further comprising an antiviral additive, an antimicrobial, an antibiotic, or combinations thereof, wherein said antiviral additive comprises one or more of an antiviral additive that is effective against HIV and hepatitis, and wherein said antimicrobial or antibiotic comprises one or more of erythromycin, bacitracin, neomycin, penicillin, polymyxin B, tetracycline, viomycin, chloromycetin, streptomycin, cefazolin, ampicillin, azactam, tobramycin, clindamycin, or gentamycin.

21. The composition of claim 16, further comprising living cells.

22. The composition of claim 21, wherein the living cells comprise chondrocytes, platelets, blood plasma, bone marrow cells, mesenchymal stem cells, pluripotential cells, osteoblasts, fibroblasts, or combinations thereof.

23. The composition of claim 22, wherein the living cells are present in an amount ranging from $10^5$ to $10^8$ per cc of the carrier.

24. The composition of claim 16, wherein the composition is a putty.

25. A composition for application to a bone defect site comprising bioactive glass and a fluid carrier, wherein said bioactive glass comprises glass particles ranging from 90 μm to 710 μm in size and glass powder ranging from 32 μm to 90 μm in size, wherein said glass particles and said glass powder are present in a ratio of glass particles to glass powder ranging from about 3.5:1 to about 5:1, and wherein said bioactive glass is present in an amount ranging from about 68% to about 70% (w/w) of the composition; wherein the carrier comprises a mixture of glycerol and polyethylene glycol, wherein the carrier is present in an amount ranging from about 30% to about 32% (w/w) of the composition, and wherein said glycerol and said polyethylene glycol are present in a ratio of glycerol to polyethylene glycol ranging from about 45:55 to about 65:35; and wherein the composition is malleable during application of the composition to the bone defect.

26. The composition of claim 25, wherein said polyethylene glycol has a molecular weight ranging from 1000 to 2000 Daltons.

27. The composition of claim 25, further comprising living cells.

28. The composition of claim 27, wherein the living cells comprise chondrocytes, platelets, blood plasma, bone marrow cells, mesenchymal stem cells, pluripotential cells, osteoblasts, fibroblasts, or combinations thereof.

29. The composition of claim 28, wherein the living cells are present in an amount ranging from $10^5$ to $10^8$ per cc of the carrier.

30. The composition of claim 25, wherein said composition has been sterilized by gamma radiation.

31. The composition of claim 25, wherein the composition is a putty.

* * * * *